(12) United States Patent
Van Den Eynde et al.

(10) Patent No.: US 9,549,553 B2
(45) Date of Patent: Jan. 24, 2017

(54) ACTIVE COMPOUND COMBINATIONS HAVING INSECTICIDAL PROPERTIES

(71) Applicant: BAYER CROPSCIENCE AKTIENGESELLSCHAFT, Monheim am Rhein (DE)

(72) Inventors: Koen Van Den Eynde, Beijing (CN); Wolfgang Thielert, Odenthal (DE)

(73) Assignee: BAYER CROPSCIENCE AKTIENGESELLSCHAFT, Monheim am Rhein (DE)

(*) Notice: Subject to any disclaimer, the term of this patent is extended or adjusted under 35 U.S.C. 154(b) by 0 days.

(21) Appl. No.: 14/784,357

(22) PCT Filed: Apr. 15, 2014

(86) PCT No.: PCT/EP2014/057624
§ 371 (c)(1),
(2) Date: Oct. 14, 2015

(87) PCT Pub. No.: WO2014/170328
PCT Pub. Date: Oct. 23, 2014

(65) Prior Publication Data
US 2016/0058003 A1 Mar. 3, 2016

(30) Foreign Application Priority Data

Apr. 19, 2013 (EP) .................................... 13164448
May 29, 2013 (EP) .................................... 13169621

(51) Int. Cl.
*A01N 37/46* (2006.01)
*A01N 37/34* (2006.01)
*A01N 37/30* (2006.01)
*A01N 53/08* (2006.01)
*A01N 53/00* (2006.01)

(52) U.S. Cl.
CPC ............... *A01N 37/34* (2013.01); *A01N 37/30* (2013.01); *A01N 53/00* (2013.01)

(58) Field of Classification Search
CPC combination set(s) only.
See application file for complete search history.

(56) References Cited

U.S. PATENT DOCUMENTS

| | | | |
|---|---|---|---|
| 2006/0063724 A1 | 3/2006 | Konze et al. | |
| 2013/0005712 A1 | 1/2013 | Sakata et al. | |

FOREIGN PATENT DOCUMENTS

| | | | |
|---|---|---|---|
| EP | 0919542 A2 | 6/1999 | |
| JP | 2003012415 A | 1/2003 | |
| WO | 2004018410 A1 | 3/2004 | |
| WO | 2008037378 A2 | 4/2008 | |
| WO | 2010012442 A2 | 2/2010 | |
| WO | 2012034472 A1 | 3/2012 | |

OTHER PUBLICATIONS

International Search Report and Written Opinion from corresponding PCT/EP2014/057624, mailed Jul. 16, 2014.

*Primary Examiner* — John Pak
(74) *Attorney, Agent, or Firm* — McBee Moore Woodward Vanik IP LLC

(57) ABSTRACT

The present invention relates to novel active compound combinations comprising at least one known compound of the formula (I)

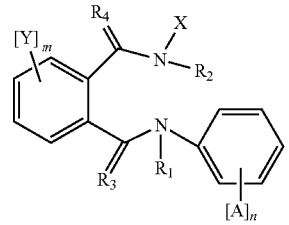

in which X, $R_1$ to $R_4$, A, n, Y, and m are as defined in the description, and at least one further known active compound from the class of the pyrethroids, which combinations are highly suitable for controlling animal pests such as insects and unwanted acarids.

16 Claims, No Drawings

ACTIVE COMPOUND COMBINATIONS HAVING INSECTICIDAL PROPERTIES

CROSS REFERENCE TO RELATED APPLICATIONS

This application is a §371 National Stage Application of PCT/EP2014/057624, filed 15 Apr. 2014, which claims priority to EP 13164448.6, filed 19 Apr. 2013 and EP 13169621.3, filed 29 May 2013.

BACKGROUND

Field of the Invention

The present invention relates to novel active compound combinations comprising firstly at least one known compound of the formula (I) and secondly at least one further active compound from the class of pyrethroids, which combinations are highly suitable for controlling animal pests, such as insects and unwanted acarids.

Description of Related Art

It is known that phthalic acid amides (Ryanodine receptor inhibitors class) have insecticidal activity (see, e.g., EP 0 919 542, WO 2004/018410 or WO 2010/012442). Cyano group containing phthalic acid amide-based compounds and their preparation are further disclosed in WO 2012/034472.

Furthermore, it is already known that numerous heterocycles, organotin compounds, benzoyl-ureas and pyrethroids have insecticidal and acaricidal properties. However, the activity of these compounds is not always satisfactory.

SUMMARY

A first aspect refers to an active compound combination comprising at least one compound of the formula (I-1)

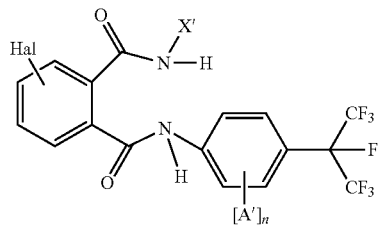

wherein
Hal represents F, Cl, I or Br; and
X' represents $C_1$-$C_6$ alkyl or substituted $C_1$-$C_6$ alkyl having at least one substituent selected from the group consisting of halogen, hydroxy, cyano, nitro, amino, halo $C_1$-$C_3$ alkyl group, preferably $C_1$-$C_6$ haloalkyl;
A' represents $C_1$-$C_3$ alkyl, $C_1$-$C_3$ haloalkyl, halogen;
n represents 0, 1, 2, 3 or 4, preferably 0, 1 or 2;
and at least one compound selected from the group consisting of (II-11) beta-Cyfluthrin, (II-13) lambda-Cyhalothrin, and (II-21) Deltamethrin.

One embodiment refers to said active compound combination wherein compound of formula (I) is compound (I-5).

Another aspect refers to the use of an active compound combination according to the invention for controlling animal pests.

Another aspect refers to a method for controlling animal pests, characterized in that an active compound combination according of the invention is allowed to act on animal pests and/or their habitat and/or seed.

One embodiment refers to said method characterized in that an active compound of the formula I and one of the active compounds (II-1), (II-2), (II-3), or (II-4) are allowed to act simultaneously on seed.

Another aspect refers to a process for preparing insecticidal and acaricidal compositions, characterized in that an active compound combination according to the invention is mixed with extenders and/or surfactants.

Further aspects refer to the use of an active compound combination according to the invention for treating seed or for treating transgenic plants or, more specifically, for treating seed of transgenic plants.

Another aspect refers to a seed treated with an active compound combination according to the invention.

Yet another aspect refers to a seed wherein a compound of formula (I-1) as described herein and a compound selected from compounds (II-1), (II-2), (II-3), or (II-4) as described herein are present in one or different layers on the seed, a coating or as a further layer or further layers in addition to a coating.

DETAILED DESCRIPTION OF A PREFERRED EMBODIMENT

It has now been found that active compound combinations of at least one compound of the formula (I)

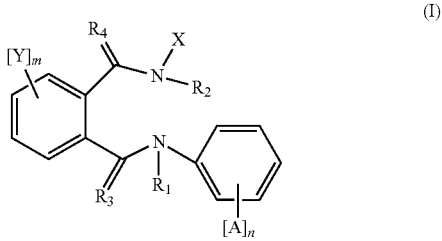

wherein
A represents individually halogen, cyano, nitro, hydroxyl, amino, $C_1$-$C_8$ alkyl group, substituted $C_1$-$C_8$ alkyl group having at least one substituent elected from the group consisting of halogen, hydroxy, cyano, nitro, amino, halo $C_1$-$C_3$ alkyl group, $C_1$-$C_3$ alkoxy group, halo $C_1$-$C_3$ alkoxy group, $C_1$-$C_3$ alkylthio group, halo $C_1$-$C_3$ alkylthio group, $C_1$-$C_3$ alkylsulfinyl group, halo $C_1$-$C_3$ alkylsulfinyl group, $C_1$-$C_3$ alkylsulfonyl group, halo $C_1$-$C_3$ alkylsulfonyl group and $C_1$-$C_3$ alkylthio, $C_1$-$C_3$ alkyl group; further, an arbitrary saturated carbon atom in said optionally substituted $C_1$-$C_8$ alkyl group;
n represents 0, 1, 2, 3 or 4, preferably 0, 1 or 2;
$R_1$ represents hydrogen, halogen, cyano $C_1$-$C_8$ alkyl or $C_1$-$C_8$ haloalkyl;
$R_2$ represents hydrogen, halogen, cyano $C_1$-$C_8$ alkyl or $C_1$-$C_8$ haloalkyl;
$R_3$ represents O or S;
$R_4$ represents O or S;
Y represents individually hydrogen, halogen, cyano, nitro, $C_1$-$C_6$ alkyl group, halo $C_1$-$C_6$ alkyl group, $C_2$-$C_6$ alkenyl group, halo $C_2$-$C_6$ alkenyl group, $C_2$-$C_6$ alkynyl group, halo $C_2$-$C_6$ alkynyl group, $C_3$-$C_6$ cycloalkyl group, halo $C_3$-$C_6$ cycloalkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, or halo $C_1$-$C_6$ alkylsulfonyl group;

m represents 0, 1, 2, 3, or 4;

X represents a $C_1$-$C_8$ alkyl group or a substituted $C_1$-$C_8$ alkyl group having at least one substituent selected from the group consisting of halogen, hydroxy, cyano, nitro, amino, halo $C_1$-$C_3$ alkyl group, $C_1$-$C_3$ alkoxy group, halo $C_1$-$C_3$ alkoxy group;

and at least one of the active compounds from group (II), selected from pyrethroids, e.g. Acrinathrin (II-1), Allethrin (II-2), d-cis-trans Allethrin (II-3), d-trans Allethrin (II-4), Bifenthrin (II-5), Bioallethrin (II-6), Bioallethrin S-cyclopentenyl isomer (II-7), Bioresmethrin (II-8), Cycloprothrin (II-9), Cyfluthrin (II-10), beta-Cyfluthrin (II-11), Cyhalothrin (II-12), lambda-Cyhalothrin (II-13), gamma-Cyhalothrin (II-14), Cypermethrin (II-15), alpha-Cypermethrin (II-16), beta-Cypermethrin (II-17), theta-Cypermethrin (II-18), zeta-Cypermethrin (II-19), Cyphenothrin [(1R)-trans isomers] (II-20), Deltamethrin (II-21), Empenthrin [(EZ)-(1R) isomers) (II-22), Esfenvalerate (II-23), Etofenprox (II-24), Fenpropathrin (II-25), Fenvalerate (II-26), Flucythrinate (II-27), Flumethrin (II-28), tau-Fluvalinate (II-29), Halfenprox (II-30), Imiprothrin (II-31), Kadethrin (II-32), Permethrin (II-33), Phenothrin [(1R)-trans isomer) (II-34), Prallethrin (II-35), Pyrethrine (pyrethrum) (II-36), Resmethrin (II-37), Silafluofen (II-38), Tefluthrin (II-39), Tetramethrin (II-40), Tetramethrin [(1R) isomers)] (II-41), Tralomethrin (II-42), and Transfluthrin (II-43) are synergistically active and suitable for controlling animal pests.

Surprisingly, the insecticidal activity of the active compound combination according to the invention is considerably higher than the sum of the activities of the individual active compounds. An unforeseeable true synergistic effect is present, and not just an addition of activities.

In addition to at least one active compound of the formula (I), the active compound combinations according to the invention comprise at least one of the active compounds (II-1) to (II-43) listed above.

In a preferred embodiment of the present invention, the compounds of the general formula (I) is represented by compounds of formula (I-1):

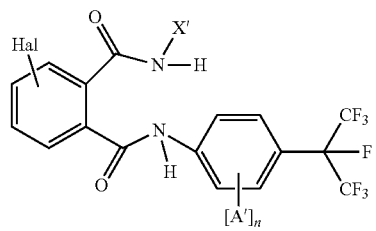

(I-1)

wherein
Hal represents F, Cl, I or Br; and
X' represents $C_1$-$C_6$ alkyl or substituted $C_1$-$C_6$ alkyl having at least one substituent selected from the group consisting of halogen, hydroxy, cyano, nitro, amino, halo $C_1$-$C_3$ alkyl group, preferably a $C_1$-$C_6$ cyanoalkyl;
A' represents $C_1$-$C_3$ alkyl, $C_1$-$C_3$ haloalkyl, halogen, preferably methyl, halomethyl, ethyl or haloethyl, more preferably methyl or ethyl;
n represents 0, 1, 2, 3 or 4, preferably 0, 1 or 2, more preferably 1.

According to the invention, "alkyl" represents straight-chain or branched aliphatic hydrocarbons having 1 to 8, preferably 1 to 6, more preferably 1 to 3, carbon atoms. Suitable alkyl groups are, for example, methyl, ethyl, n-propyl, i-propyl, n-, iso-, sec- or tert-butyl, pentyl or hexyl. The alkyl group may be unsubstituted or is substituted by at least one of the substituents mentioned here.

According to the invention, "halogen" or "Hal" represents fluorine, chlorine, bromine or iodine, preferably fluorine, chlorine or bromine.

According to the invention, "haloalkyl" represents alkyl groups having up to 8 carbon atoms in which at least one hydrogen atom has been replaced by a halogen. Suitable haloalkyl groups are, for example, $CH_2F$, $CHF_2$, $CF_3$, $CF_2Cl$, $CFCl_2$, $CCl_3$, $CF_2Br$, $CF_2CF_3$, $CFHCF_3$, $CH_2CF_3$, $CH_2CH_2F$, $CH_2CHF_2$, $CFClCF_3$, $CCl_2CF_3$, $CF_2CH_3$, $CF_2CH_2F$, $CF_2CHF_2$, $CF_2CF_2Cl$, $CF_2CF_2Br$, $CFHCH_3$, $CFHCHF_2$, $CHFCF_3$, $CHFCF_2Cl$, $CHFCF_2Br$, $CFClCF_3$, $CCl_2CF_3$, $CF_2CF_2CF_3$, $CH_2CH_2CH_2F$, $CH_2CHFCH_3$, $CH_2CF_2CF_3$, $CF_2CH_2CF_3$, $CF_2CF_2CH_3$, $CHFCF_2CF_3$, $CF_2CHFCF_3$, $CF_2CF_2CHF_2$, $CF_2CF_2CH_2F$, $CF_2CF_2CF_2Cl$, $CF_2CF_2CF_2Br$, 1,2,2,2-tetrafluoro-1-(trifluoromethyl)ethyl, 2,2,2-trifluoro-1-(trifluoromethyl)ethyl, pentafluoroethyl, 1-(difluoromethyl)-1,2,2,2-tetrafluoroethyl, 2-bromo-1,2,2-trifluoro-1-(trifluoromethyl)ethyl, 1-(difluoromethyl)-2,2,2-trifluoroethyl. The haloalkyl group may be unsubstituted or is substituted by at least one of the substituents mentioned here.

In a more preferred embodiment of the present invention, a composition comprises at least one compound of the general formula (I) selected from the group consisting of compound (I-2), (I-3), (I-4) or (I-5):

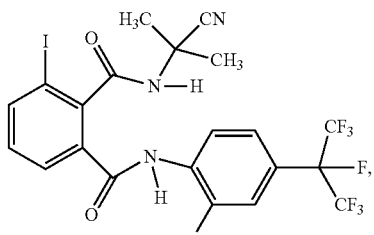

(I-2)

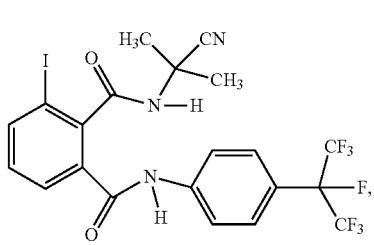

(I-3)

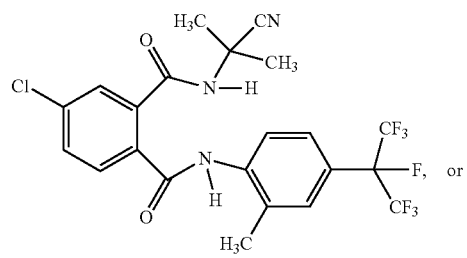

(I-4) or

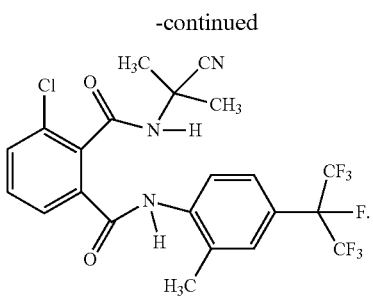

(I-5)

Even more preferably, a compound of formula (I) is selected from the group consisting of compound (I-2) or compound (I-5).

In one preferred embodiment, the compound of formula (I) is compound (I-5).

Preferably, the active compound combinations according to the invention comprise at least one compound of formula (I) such as compounds (I-2), (I-3), (I-4) or (I-5) and at least one of the active compounds (II-11) beta-Cyfluthrin, (II-13) lambda-Cyhalothrin, or (II-21) Deltamethrin.

Specifically, we found the combinations listed in Table 1, where each combination is per se a preferred embodiment according to the invention.

TABLE 1

| Mixture comprising |
|---|
| I-2 and (II-11) beta-Cyfluthrin |
| I-3 and (II-11) beta-Cyfluthrin |
| I-4 and (II-11) beta-Cyfluthrin |
| I-5 and (II-11) beta-Cyfluthrin |
| I-2 and (II-13) lambda-Cyhalothrin |
| I-3 and (II-13) lambda-Cyhalothrin |
| I-4 and (II-13) lambda-Cyhalothrin |
| I-5 and (II-13) lambda-Cyhalothrin |
| I-2 and (II-21) Deltamethrin |
| I-3 and (II-21) Deltamethrin |
| I-4 and (II-21) Deltamethrin |
| I-5 and (II-21) Deltamethrin |

The synergistic effect is particularly pronounced when the active compounds in the active compound combinations according to the invention are present in certain weight ratios. However, the weight ratios of the active compounds in the active compound combinations can be varied within a relatively wide range. In general, the combinations according to the invention comprise an active compound of the formula (I) and one of the active compounds (II-1) to (II-43) in the following preferred and particularly preferred mixing ratios:

Preferred mixing ratio: 125:1 to 1:125
More preferred mixing ratio: 40:1 to 1:40
Particularly preferred mixing ratio: 25:1 to 1:25

In the range of 25:1 to 1:25, mixing ratios are, e.g. 20:1 to 1:20, 15:1 to 1:15, 10:1 to 1:10, 5:1 to 1:5, 3:1 to 1:3, 2:1 to 1:2 or combinations thereof such as 20:1 to 1:5 or 5:1 to 1:3.

The mixing ratios are based on weight ratios. The ratio is to be understood as meaning active compound of the formula (I): active compound of group (II) preferably compound (II-11), (II-13) or (II-21).

For example, preferred mixing ratios for combinations of compound (I-5) and beta-Cyfluthrin are 25:1 to 1:5, even more preferred 25:1 to 1:1, e.g., 25:1 to 5:1.

For example, preferred mixing ratios for combinations of compound (I-5) and Deltamethrin are 100:1 to 1:5, even more preferred 100:1 to 1:1, e.g., 50:1 to 5:1.

For example, preferred mixing ratios for combinations of compound (I-5) and lambda-Cyhalothrin are 40:1 to 1:4, even more preferred 35:1 to 1:4, e.g., 10:1 to 1:4.

The active compound combinations according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include pests: from the order of the Anoplura (Phthiraptera), from the class of the Arachnida, from the class of the Bivalva, from the order of the Chilopoda, from the order of the Coleoptera, from the order of the Collembola, from the order of the Dermaptera, from the order of the Diplopoda, from the order of the Diptera, from the class of the Gastropoda, from the class of the helminths, it is furthermore possible to control protozoa, from the order of the Heteroptera, from the order of the Homoptera, from the order of the Hymenoptera, from the order of the Isopoda, from the order of the Isoptera, from the order of the Lepidoptera, from the order of the Orthoptera, from the order of the Siphonaptera, from the order of the Symphyla, from the order of the Thysanoptera, from the order of the Thysanura, phytoparasitic nematodes.

If appropriate, the active compound combinations according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (*Mycoplasma*-like organisms) and RLO (*Rickettsia*-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits and seeds and also roots, tubers and rhizomes. The plant parts also include harvested material, and vegetative and generative propagation material, for example cuttings, tubers, rhizomes, offshoots and seeds.

Treatment according to the invention of the plants and plant parts with the active compound combinations is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

The active compound combinations according to the invention are particularly suitable for treating seed. Here, the combinations according to the invention mentioned above as preferred or particularly preferred may be mentioned as being preferred. Thus, a large part of the damage to crop plants which is caused by pests occurs as early as when the seed is attacked during storage and after the seed is introduced into the soil, and during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of pests by treating the seeds of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants. It is furthermore desirable to optimize the amount of active compound employed in such a way as to provide maximum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and also the germinating plant with a minimum of crop protection agents being employed.

Accordingly, the present invention relates in particular also to a method for protecting seed and germinating plants against attack by pests which comprises treating the seed with an active compound combination according to the invention. The method according to the invention for protecting seed and germinating plants against attack by pests comprises a method wherein the seed is treated simultaneously with an active compound of the formula I and one of the active compounds (II-1) to (II-43). The invention also comprises a method wherein the seed is treated at different times with an active compound of the formula I and one of the active compounds (II-1) to (11-43). The invention also relates to the use of the active compound combinations according to the invention for treating seed for protecting the seed and the plant emerging therefrom against pests. Furthermore, the invention relates to seed treated with an active compound combination according to the invention for protection against pests. The invention also relates to seed treated simultaneously with an active compound of the formula I and one of the active compounds (II-1) to (II-43). The invention furthermore relates to seed treated at different times with an active compound of the formula I and one of the active compounds (II-1) to (II-43). In the case of seed treated at different times with an active compound of the formula I and one of the active compounds (II-1) to (II-43), the individual active compounds of the composition according to the invention, may be present in different layers on the seed. Here, the layers comprising an active compound of the formula I and one of the active compounds (II-1) to (II-43) may optionally be separated by an intermediate layer. The invention also relates to seed where an active compound of the formula I and one of the active compounds (II-1) to (II-43) are applied as component of a coating or as a further layer or further layers in addition to a coating.

One of the advantages of the present invention is that the particular systemic properties of the active compound combinations according to the invention mean that treatment of the seed with these active compound combinations not only protects the seed itself, but also the resulting plants after emergence, from pests. In this manner, the immediate treatment of the crop at the time of sowing or shortly thereafter can be dispensed with.

A further advantage is the synergistically increased insecticidal activity of the active compound combinations according to the invention in comparison with the insecticidal individual active compound, which exceeds the expected activity of the two active compounds when applied individually. Also advantageous is the synergistically increased fungicidal activity of the active compound combinations according to the invention in comparison with the fungicidal individual active compound, which exceeds the expected activity of the active compound when applied individually. This makes possible an optimization of the amount of active compounds employed.

It is likewise to be considered as advantageous that the active compound combinations according to the invention can be employed also in particular in transgenic seed, the plants arising from this seed being capable of expressing a protein directed against pests. By treating such seed with the active compound combinations according to the invention, certain pests can be controlled merely by the expression of the, for example, insecticidal protein, and additionally be protected by the active compound combinations according to the invention against damage.

The active compound combinations according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, sorghum and millet, wheat, barley, oats, rye, sunflower, tobacco, potatoes or vegetables (for example tomatoes, cabbage plants). The active compound combinations according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with an active compound combination according to the invention is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from *Bacillus thuringiensis*.

In the context of the present invention, the active compound combination according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the active compound combination according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The active compound combinations can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are: for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound combinations according to the invention, in commercially available formulations and in the use forms prepared from these formulations, can be present in a mixture with other active compounds such as insecticides, attractants, sterilants, bactericides, acaricides, nematicides, fungicides, growth regulators or herbicides. The insecticides include, for example, phosphoric esters, carbamates, carboxylic esters, chlorinated hydrocarbons, phenylureas, substances produced by microorganisms, and the like.

A mixture with other known active compounds, such as herbicides, or with fertilizers and growth regulators is also possible.

When used as insecticides, the active compound combinations according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.00000001 to 95% by weight of active compound, preferably between 0.00001 and 1% by weight.

Application is in a manner appropriate for the use forms.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The plants listed can be treated in a particularly advantageous manner with the active compound combinations according to the invention. The preferred ranges stated above for the active compound combinations also apply to the treatment of these plants. Particular emphasis is given to the treatment of plants with the active compound combinations specifically mentioned in the present text.

The active compound combinations according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, from the order of the Mallophagida and the suborders Amblycerina and Ischnocerina, from the order of the Diptera and the suborders Nematocerina and Brachycerina, from the order of the Siphonapterida, from the order of the Heteropterida, from the order of the Blattarida, from the subclass of the Acari (Acarina) and the orders of the Meta- and Mesostigmata, from the order of the Actinedida (Prostigmata) and Acaridida (Astigmata).

The active compound combinations according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compound combinations according to the invention.

The active compound combinations according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compounds, such as collars, ear marks, tail marks, limb bands, halters, marking devices and the like.

When used for cattle, poultry, pets and the like, the active compound combinations can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the active compound combinations according to the invention have a strong insecticidal action against insects which destroy industrial materials.

The following insects may be mentioned as examples and as preferred—but without any limitation: Beetles, Hymenopterons, Termites, Bristletails.

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The active compound combinations according to the invention can likewise be employed for protecting objects which come into contact with seawater or brackish water, in particular hulls, screens, nets, buildings, moorings and signalling systems, against fouling.

Furthermore, the active compound combinations according to the invention, alone or in combinations with other active compounds, may be employed as antifouling agents.

In domestic, hygiene and stored-product protection, the active compound combinations are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, Acarina, Araneae, Opiliones, Isopoda, Diplopoda, Chilopoda, Zygentoma, Blattaria, Saltatoria, Dermaptera, Isoptera, Psocoptera, Coleoptera, Diptera, Lepidoptera, Siphonaptera, Hymenoptera, Anoplura, Heteroptera.

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The good insecticidal and acaricidal activity of the active compound combinations according to the invention is illustrated by the examples below. Whereas the individual active compounds show weaknesses in their activity, the combinations show an activity which exceeds a simple addition of activities.

A synergistic effect in insecticides and acaricides is always present when the activity of the active compound combinations exceeds the total of the activities of the active compounds when applied individually.

The expected activity for a given combination of two active compounds can be calculated according to S. R. Colby, Weeds 15 (1967), 20-22 as follows:

If

X is the efficacy expressed in % mortality of the untreated control for test compound A at a concentration of m ppm respectively m g/ha, Y is the efficacy expressed in % mortality of the untreated control for test compound B at a concentration of n ppm respectively n g/ha, E is the efficacy expressed in % mortality of the untreated control using the mixture of A and B at m and n ppm respectively m and n g/ha, then is $$E = X + Y - \frac{X \times Y}{100}$$

If the observed insecticidal efficacy of the combination is higher than the one calculated as "E", then the combination of the two compounds is more than additive, i.e., there is a synergistic effect.

The invention is illustrated by the examples below. However, the invention is not limited to the examples.

Example A

*Spodoptera frugiperda*—Spray Test

| Solvent: | 78.0 | parts by weight acetone |
| | 1.5 | parts by weight dimethylformamide |
| Emulsifier: | 0.5 | parts by weight alkylarylpolyglycolether |

To produce a suitable preparation of the active compound, 1 part by weight of active compound is mixed with the stated amount of solvent and emulsifier, and the concentrate is diluted with emulsifier-containing water to the desired concentration. To produce a suitable preparation of a spore suspension the spores are diluted with emulsifier-containing water to the desired concentration.

Maize (*Zea mais*) leaf sections are sprayed with a preparation of the active ingredient of the desired concentration. Once dry, the leaf sections are infested with fall armyworm larvae (*Spodoptera frugiperda*).

After the specified period of time, mortality in % is determined. 100% means all caterpillars have been killed and 0% means none of the caterpillars have been killed. The mortality values determined thus are recalculated using the Colby-formula (see sheet 1).

According to the present application in this test e.g. the following combinations show a synergistic effect in comparison to the single compounds:

TABLE A

*Spodoptera frugiperda* - spray test

| Active Ingredient | Concentration in g ai/ha | Efficacy in % after $6^d$ | |
|---|---|---|---|
| (I-5) | 0.8 | 33 | |
| Beta-Cyfluthrin (II-11) | 0.032 | 0 | |
| (I-5) + Beta-Cyfluthrin (II-11) (25:1) | | obs.* | cal.** |
| according to the invention | 0.8 + 0.032 | 67 | 33 |
| (I-5) | 3 | 33 | |
| | 0.25 | 0 | |
| Deltamethrin | 0.25 | 0 | |
| (I-5) + Deltamethrin (1:1) | | obs.* | cal.** |
| according to the invention | 0.25 + 0.25 | 67 | 0 |

*obs. = observed insecticidal efficacy,
**cal. = efficacy calculated with Colby-formula Example B-1

*Phaedon cochleariae*—Spray Test

| Solvent: | 78.0 | parts by weight of acetone |
| | 1.5 | parts by weight of dimethylformamide |
| Emulsifier: | 0.5 | parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration. To produce a suitable preparation of a spore suspension the spores are diluted with emulsifier-containing water to the desired concentration.

Chinese cabbage (*Brassica pekinensis*) leaf-disks are sprayed with a preparation of the active ingredient of the desired concentration. Once dry, the leaf disks are infested with mustard beetle larvae (*Phaedon cochleariae*).

After the specified period of time, mortality in % is determined. 100% means all beetle larvae have been killed and 0% means none of the beetle larvae have been killed. The mortality values determined thus are recalculated using the Colby-formula (see sheet 1).

According to the present application in this test e.g. the following combinations show a synergistic effect in comparison to the single compounds:

TABLE B

Phaedon cochleariae - spray test

| Active Ingredient | Concentration in g ai/ha | Efficacy in % after $6^d$ | |
|---|---|---|---|
| (I-5) | 12 | 0 | |
|  | 2.5 | 0 | |
| Lambda-Cyhalothrin | 0.25 | 0 | |
| (I-5) + Lambda-Cyhalothrin (10:1) |  | obs.* | cal.** |
| according to the invention | 2.5 + 0.25 | 50 | 0 |

*obs. = observed insecticidal efficacy,
**cal. = efficacy calculated with Colby-formula

Example B-2

*Phaedon cochleariae*—Spray Test

Solvent: 7 parts by weight of dimethylformamide
Emulsifier: alkylaryl polyglycol ether To produce a suitable preparation of active compound, 1 part by weight of active compound is mixed with the stated amount of solvent and is diluted with water, containing an emulgator concentration of 1000 ppm, to the desired concentration. Further test concentrations are prepared by dilution with emulsifier containing water Ammonium salt and/or penetration enhancer in a dosage of 1000 ppm are added to the desired concentration if necessary.

Cabbage leaves (*Brassica oleracea*) are treated by being sprayed with the preparation of the active compound of the desired concentration and are infested with mustard beetle larvae (*Phaedon cochleariae*).

After the specified period of time mortality in % is determined. 100% means all the beetle larvae have been killed and 0% means none of the beetle larvae have been killed. The mortality values determined thus are recalculated using the Colby-formula (see sheet 1).

According to the present application in this test e.g. the following combinations show a synergistic effect in comparison to the single compounds:

TABLE C

Phaedon cochleariae - spray test

| Active Ingredient | Concentration in ppm | Efficacy in % after $3^d$ | |
|---|---|---|---|
| (I-5) | 4.8 | 50 | |
|  | 1.2 | 0 | |
| β-Cyfluthrin | 1.2 | 0 | |
| (I-5) + β-Cyfluthrin (1:1) |  | obs.* | cal.** |
| according to the invention | 1.2 + 1.2 | 40 | 0 |

*obs. = observed insecticidal efficacy,
**cal. = efficacy calculated with Colby-formula

Example C-1

*Myzus persicae*—Spray Test

| Solvent: | 78.0 | parts by weight acetone |
|---|---|---|
|  | 1.5 | parts by weight dimethylformamide |
| Emulsifier: | 0.5 | parts by weight alkylarylpolyglycolether |

To produce a suitable preparation of active compound, 1 part by weight of active compound is mixed with the stated amount of solvent and emulsifier, and the concentrate is diluted with emulsifier-containing water to the desired concentration.

Chinese cabbage (*Brassica pekinensis*) leaf-disks infected with all instars of the green peach aphid (*Myzus persicae*) are sprayed with a preparation of the active ingredient of the desired concentration.

After the specified period of time, mortality in % is determined 100% means all aphids have been killed; 0% means none of the aphids have been killed. The mortality values determined thus are recalculated using the Colby-formula (see sheet 1).

According to the present application in this test e.g. the following combinations show a synergistic effect in comparison to the single compounds:

TABLE C-1

Myzus persicae - spray test

| Active Ingredient | Concentration in g ai/ha | Efficacy in % after $6^d$ | |
|---|---|---|---|
| (I-5) | 15 | 0 | |
|  | 1.5 | 0 | |
|  | 1.25 | 0 | |
| Deltamethrin | 0.15 | 0 | |
| (I-5) + Deltamethrin (100:1) |  | obs.* | cal.** |
| according to the invention | 15 + 0.15 | 70 | 0 |
| Lambda-Cyhalothrin | 0.125 | 0 | |
| (I-5) + Lambda-Cyhalothrin (10:1) |  | obs.* | cal.** |
| according to the invention | 1.25 + 0.125 | 70 | 0 |

*obs. = observed insecticidal efficacy,
**cal. = efficacy calculated with Colby-formula

Example C-2

*Myzus persicae*—Spray Test

Solvent: 7 parts by weight of dimethylformamide
Emulsifier: alkylaryl polyglycolether To produce a suitable preparation of active compound, 1 part by weight of active compound is mixed with the stated amount of solvent and is diluted with water, containing an emulgator concentration of 1000 ppm, to the desired concentration. Further test concentrations are prepared by dilution with emulsifier containing water Ammonium salt and/or penetration enhancer in a dosage of 1000 ppm are added to the desired concentration if necessary.

Cabbage leaves (*Brassica oleracea*) which are heavily infested by the green peach aphid (*Myzus persicae*) are treated by being sprayed with the preparation of the active compound of the desired concentration.

After the specified period of time, mortality in % is determined 100% means all the aphids have been killed; 0% means none of the aphids have been killed. The mortality values determined thus are recalculated using the Colby-formula (see sheet 1).

According to the present application in this test e.g. the following combinations show a synergistic effect in comparison to the single compounds:

TABLE C-2

| | Myzus persicae- spray test | | |
|---|---|---|---|
| Active Ingredient | Concentration in ppm | Efficacy in % after 6$^d$ | |
| (5:1) | 2.5 | 0 | |
| β-Cyfluthrin | 0.5 | 50 | |
| (5:1) + β-Cyfluthrin (5:1) | | obs.* | cal.** |
| according to the invention | 2.5 + 0.5 | 80 | 50 |

*obs. = observed insecticidal efficacy,
**cal. = efficacy calculated with Colby-formula

Example D

*Tetranychus urticae*—Spray Test, OP-Resistant

| Solvent: | 78.0 | parts by weight acetone |
|---|---|---|
| | 1.5 | parts by weight dimethylformamide |
| Emulsifier: | 0.5 | parts by weight alkylarylpolyglycolether |

To produce a suitable preparation of active compound, 1 part by weight of active compound is mixed with the stated amount of solvent and emulsifier, and the concentrate is diluted with emulsifier-containing water to the desired concentration. To produce a suitable preparation of a spore suspension the spores are diluted with emulsifier-containing water to the desired concentration.

French beans (*Phaseolus vulgaris*) which are heavily infested with all stages of the two spotted spidermite (*Tetranychus urticae*), are sprayed with a preparation of the active ingredient of the desired concentration.

After the specified period of time, mortality in % is determined. 100% means all spider mites have been killed and 0% means none of the spider mites have been killed. The mortality values determined thus are recalculated using the Colby-formula (see sheet 1).

According to the present application in this test e.g. the following combinations show a synergistic effect in comparison to the single compounds:

TABLE D

| | Tetranychus urticae - spray test | | |
|---|---|---|---|
| Active Ingredient | Concentration in g ai/ha | Efficacy in % after 6$^d$ | |
| (I-5) | 10 | 0 | |
| | 2 | 0 | |
| Lambda-Cyhalothrin | 1 | 0 | |
| (I-5) + Lambda-Cyhalothrin (10:1) | | obs.* | cal.** |
| according to the invention | 10 + 1 | 50 | 0 |

*obs. = observed insecticidal efficacy,
**cal. = efficacy calculated with Colby-formula

Example E

*Plutella xylostella*—Spray Test

| Solvent: | 7 | parts by weight of dimethylformamide |
|---|---|---|
| Emulsifier: | 2 | parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration Ammonium salt and/or penetration enhancer in a dosage of 1000 ppm are added to the desired concentration if necessary.

Cabbage leaves (*Brassica oleracea*) are treated by being sprayed with the preparation of the active compound of the desired concentration and are infested with larvae of the diamondback moth (*Plutella xylostella*).

After the specified period of time, the mortality in % is determined. 100% means all the caterpillars have been killed; 0% means none of the caterpillars have been killed. The mortality values determined thus are recalculated using the Colby-formula (see sheet 1).

According to the present application in this test e.g. the following combinations show a synergistic effect in comparison to the single compounds:

TABLE E

| | Plutella xylostella - spray test | | |
|---|---|---|---|
| Active Ingredient | Concentration in ppm | Efficacy in % after 3$^d$ | |
| (I-5) | 0.25 | 0 | |
| Lambda-Cyhalothrin | 1 | 0 | |
| (I-5) + Lambda-Cyhalothrin (1:4) | | obs.* | cal.** |
| according to the invention | 0.25 + 1 | 92 | 0 |

*obs. = observed insecticidal efficacy,
**cal. = efficacy calculated with Colby-formula

The invention claimed is:

1. An active compound composition comprising a compound of formula (I-5)

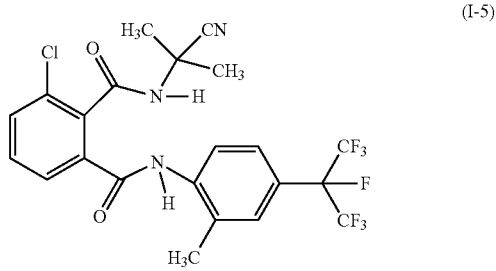 [SMILES: Cc1cc(C(F)(C(F)(F)F)C(F)(F)F)ccc1NC(=O)c1cccc(Cl)c1C(=O)NC(C)(C)C#N]

(I-5)

and at least one compound selected from the group consisting of

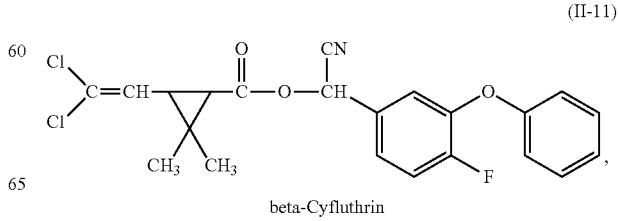

(II-11)

beta-Cyfluthrin

-continued (II-13)

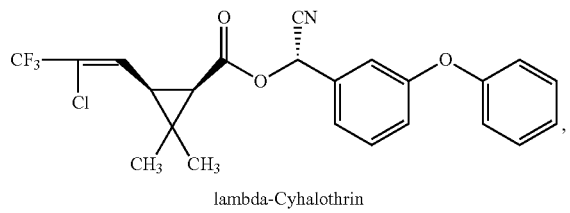

lambda-Cyhalothrin and (II-21)

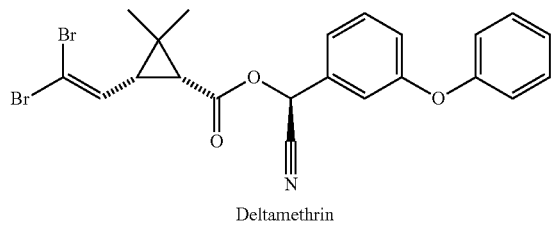

Deltamethrin wherein the weight ratio of compound (I-5) to the at least one compound is 125:1 to 1:25.

2. A composition according to claim 1, comprising (II-11) beta-Cyfluthrin.

3. A composition according to claim 2, wherein the weight ratio of compound (I-5) to compound (II-11) beta-Cyfluthrin is 25:1 to 1:5.

4. A composition according to claim 1, comprising (II-13) lambda-Cyhalothrin.

5. A composition according to claim 4, wherein the weight ratio of compound (I-5) to (II-13) lambda-Cyhalothrin is 10:1 to 1:4.

6. A composition according to claim 1, comprising (II-21) Deltamethrin.

7. A composition according to claim 6, wherein the weight ratio of compound (I-5) to (II-21) Deltamethrin is 100:1 to 1:5.

8. A composition according to claim 1, wherein (I-5) and the at least one compounds are the sole active ingredients in the composition and they are present in amounts to provide synergistic results.

9. A process for preparing an insecticidal and/or acaricidal composition, comprising mixing an active compound composition as defined in claim 1 with one or more extenders and/or surfactants.

10. Seed treated with an active compound composition according to claim 1.

11. A method for controlling pests of animals, comprising allowing a compound of formula (I-5)

(I-5)

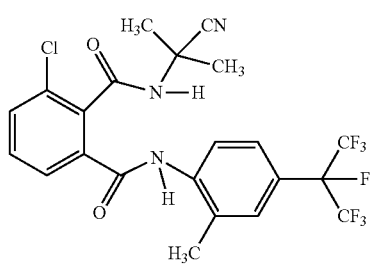

and at least one compound selected from the group consisting of (II-11)

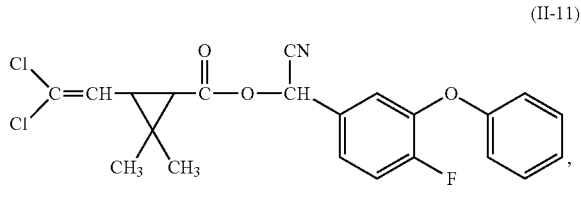

beta-Cyfluthrin (II-13)

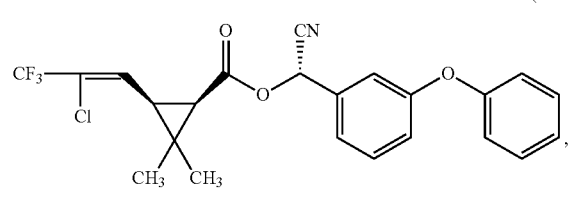

lambda-Cyhalothrin (II-21)

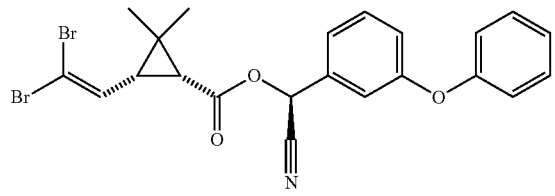

Deltamethrin wherein the weight ratio of compound (I-5) to the at least one compound is 125:1 to 1:25,
to act on one or more pests of animals and/or a habitat thereof and/or seed.

12. A method according to claim 11, wherein an active compound of formula I-5 and one of the active compounds (II-11), (II-13), or (II-21) are allowed to act simultaneously on seed.

13. A method according to claim 11, wherein an active compound of formula I-5 and one of the active compounds (II-11), (II-13), or (II-21) are allowed to act at different times on seed.

14. The method according to claim 11 comprising treating transgenic plants.

15. The method according to claim 11 comprising treating seed of transgenic plants.

16. Seed, wherein a compound of formula (I-5)

(I-5)

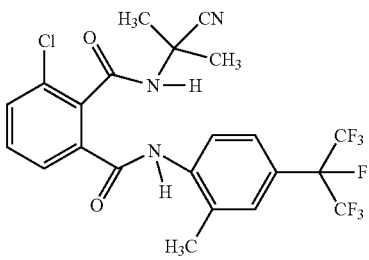

and an active compound selected from (II-11), (II-13), or (II-21)

(II-11)
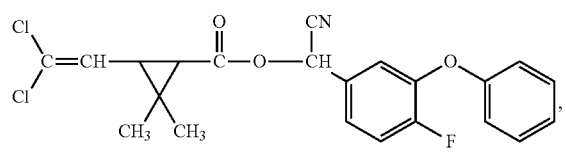
beta-Cyfluthrin
(II-13)
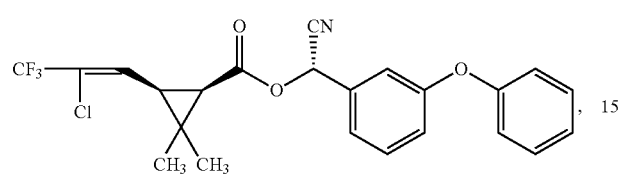
lambda-Cyhalothrin
(II-21)
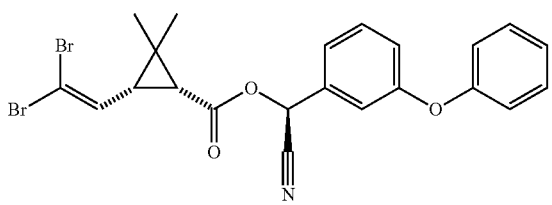
Deltamethrin
are present in one or different layers on the seed, a coating or as a further layer or further layers in addition to a coating wherein the weight ratio of (I-5) to the at least one compound is 125:1 to 1:25.
* * * * *